(12) United States Patent
Riina et al.

(10) Patent No.: US 9,775,598 B2
(45) Date of Patent: Oct. 3, 2017

(54) ANCHORED SUTURE LINE, DEVICE AND METHOD FOR SURGICAL SUTURING

(71) Applicants: Howard Antony Riina, Scarsdale, NY (US); Marvin Richard Wachs, LaGrangeville, NY (US)

(72) Inventors: Howard Antony Riina, Scarsdale, NY (US); Marvin Richard Wachs, LaGrangeville, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/793,624

(22) Filed: Jul. 7, 2015

(65) Prior Publication Data

US 2016/0015376 A1 Jan. 21, 2016

Related U.S. Application Data

(60) Provisional application No. 62/026,687, filed on Jul. 20, 2014, provisional application No. 62/071,947, filed on Jan. 4, 2015.

(51) Int. Cl.
*A61B 17/04* (2006.01)
*A61B 17/00* (2006.01)
*A61B 17/06* (2006.01)

(52) U.S. Cl.
CPC . *A61B 17/0401* (2013.01); *A61B 2017/00411* (2013.01); *A61B 2017/00862* (2013.01); *A61B 2017/00867* (2013.01); *A61B 2017/00898* (2013.01); *A61B 2017/0409* (2013.01); *A61B 2017/0417* (2013.01); *A61B 2017/06052* (2013.01); *A61B 2017/06176* (2013.01)

(58) Field of Classification Search
CPC ........... A61B 17/0401; A61B 17/0469; A61B 17/0482; A61B 17/06195; A61B 2017/0409
See application file for complete search history.

(56) References Cited

U.S. PATENT DOCUMENTS

| | | | |
|---|---|---|---|
| 4,621,638 A | 11/1986 | Silvestrini | |
| 4,744,364 A | 5/1988 | Kensey | |
| 5,417,691 A * | 5/1995 | Hayhurst | A61B 17/0401 606/139 |
| 5,571,181 A | 11/1996 | Li | |
| 7,651,505 B2 * | 1/2010 | Lubock | A61M 37/0069 600/431 |
| 8,741,354 B2 | 6/2014 | Johnson et al. | |

(Continued)

OTHER PUBLICATIONS

Written Opinion of the ISA; PCT/US2015/039440; ISA/US; Oct. 7, 2015

*Primary Examiner* — Gregory Anderson
*Assistant Examiner* — Sarah Simpson
(74) *Attorney, Agent, or Firm* — Withers Bergman LLP

(57) ABSTRACT

Anchored suture line (ASL), comprising a suture thread upon which is located a plurality of anchor structures permanently attached to said suture thread at predetermined intervals, may be advantageously employed for surgical suturing procedures. An ASL suturing device may be employed to sequentially implant the anchors, still tethered to the suture line. As they are implanted, the anchors expand thereby becoming secured in the tissue. The process may be repeated without cutting the suture line until the wound is sealed.

13 Claims, 12 Drawing Sheets

(56) References Cited

U.S. PATENT DOCUMENTS

| | | | |
|---|---|---|---|
| 8,877,233 B2 | 11/2014 | Obermiller et al. | |
| 2003/0013989 A1 | 1/2003 | Obermiller | |
| 2007/0027476 A1* | 2/2007 | Harris | A61B 17/0401 606/232 |
| 2007/0032796 A1* | 2/2007 | Chin-Chen | A61B 17/0057 606/139 |
| 2007/0185530 A1* | 8/2007 | Chin-Chen | A61B 17/0057 606/213 |
| 2009/0248071 A1* | 10/2009 | Saint | A61B 17/0401 606/232 |
| 2009/0318934 A1 | 12/2009 | Johnson et al. | |
| 2010/0076463 A1* | 3/2010 | Mavani | A61B 17/0057 606/151 |
| 2013/0030463 A1 | 1/2013 | Harris et al. | |

\* cited by examiner

ANCHORED SUTURE LINE, DEVICE AND METHOD FOR SURGICAL SUTURING

REFERENCE TO RELATED APPLICATION

This application claims the benefit of U.S. Provisional Patent Application Ser. No. 62/026,687, entitled ANCHORED SUTURE LINE AND METHOD FOR SURGICAL SUTURING, filed Jul. 20, 2014, and U.S. Provisional Patent Application 62/071,947, filed on Jan. 4, 2015, that was converted, under 37 CFR 1.53(c)(2), from U.S. Non-Provisional patent application Ser. No. 14/588,956. The contents of each are hereby incorporated by reference herein in their entirety.

BACKGROUND

Suturing is a medical procedure for the joining of biological tissues with needle and suture thread or by other means (adhesive) thereby binding tissue together to promote healing. For our purposes suturing is a process where a needle threaded with suture material is used to close an external or internal surgical opening or wound, join together two blood vessels or any two types of biological tissues with one or more stitches that pass through the bordering tissue near its edges.

Suturing, and in particular microsuturing requires great dexterity for manipulating the tissues, the needle and in tying the knot. The suturing and knot-tying procedures require the use of both hands. While suturing may be performed with a straight needle, this practice would be difficult in the microenvironment with current technology. Typically the inner surface of the tissue bordering the opening is not accessible necessitating the use of a curved needle handled with forceps and a needle holder or driver. The threaded needle is initially made to penetrate (inward) the tissue on one side of the opening and is then guided to penetrate (outward) tissue on the other side of the opening. Care must be exercised to insure that the out-of-sight needle does not undesirably penetrate nearby hidden tissue or structures. After reemergence of the needle and its attached thread, the needle may be separated from the thread and the two ends of the thread may be tied together to form a surgical no-slip knot. The reliability of the no-slip knot depends, to a large extent, on the physical properties of the suture material. It is important to keep the two tissues joined until the healing process is complete.

When multiple stitches are required to close an opening, the suturing process may be repeated providing a sequence of single individually tied stitches. This type of suture is known as an interrupted suture in that each stitch is individually knotted. Alternatively, when multiple stitches are necessary, the threaded needle may be repeatedly inserted and retrieved from the tissue and only then tied to form a single knot. This type of suture is known as continuous or "running" closure. For the same number of stitches, continuous closure may be performed more quickly than interrupted suturing. For continuous closure suturing, however, the failure of a single one of the constituent sutures or of the knot can result in the failure of the entire suture line. In addition, continuous closure does not permit individual adjustment of the tension provided by each of the suture stitches.

The tissue penetrations resulting from the suturing procedure when performed on blood vessels, ducts or other lumens, conveying blood or other bodily fluids may result in undesirable leakage. In some cases, mechanical pressure must be applied to the puncture site, for a sufficient period of time, until hemostasis occurs.

The material used for suture thread has evolved over the millennia. Suture materials may be classified as absorbable vs. non-absorbable and braided vs. non-braided (monofilament). Suture thread must simultaneously meet sometimes opposing stringent physical and biocompatibility requirements necessitating a compromise selection. For example, the surface of the suture material should have a sufficiently high coefficient of friction (i.e., rough surface) to hold a no-slip knot while simultaneously minimizing the potential for infectious agent adhesion (i.e., smooth surface).

The inventors have identified the need to develop a procedure and apparatus that can be used to perform suturing with a single hand, relax some of the requirements placed on the suture thread related to knot reliability, and simultaneously provide the benefits of interrupted suture and continuous closure suturing that can be used in both macro, microsurgical and endoscopic situations. In addition, in some procedures or situations, a need exists to facilitate the rapid sealing of the suture puncture site thereby minimizing leakage of bodily fluids.

BRIEF SUMMARY OF EMBODIMENTS

The Anchored Suture Line (ASL) surgical suturing procedure and device provides many benefits over conventional suturing techniques. ASL suturing may be performed single handedly with a single device without the need for surgical knot tying. No additional instruments are required. The ASL suturing device may be supplied preloaded with anchored suture line, sterilely packaged in a hermetically sealed envelope. ASL sutures simultaneously exhibit many advantageous features of both interrupted and continuous closure suturing. In addition, the anchored suture line can be configured to promote hemostasis at each of the suture puncture sites. The ASL suturing device is amenable to low cost manufacturing technologies and materials and can therefore be disposable.

In embodiments, there is provided a suturing apparatus comprising: an anchored suture line formed of a first biocompatible suture thread upon which is located a plurality of anchor structures permanently attached to the suture thread at predetermined intervals; the anchor structures are comprised of a second bio-compatible material, distinct from the first bio-compatible suture thread material, that can be caused to transition from a compressed state to an expanded state after implantation in biological tissue wherein the expanded state has a greater cross-sectional area than the compressed state. The anchor structures may be formed of a resilient sponge or foam, or of a material, such as, without limitation, a collagen based polymer that volumetrically expands when brought into contact with fluids. Alternatively, the anchor structures may be formed of a hollow mesh surface formed of resilient material. The anchor structures may be formed of two or more layers of distinct bio-compatible materials. In other embodiments, the anchor structures, may have an asymmetrical shape and the transition from the compressed state to the expanded state is achieved by reorientation of the asymmetrical shape. The bio-compatible suture thread may be elastic.

In further embodiments, the suturing apparatus comprises a suturing device comprising: a device body with a substantially cylindrical shape with distal and proximal faces, the device body defines a hollow cylindrical cavity about an axis of the substantially cylindrical shape, the hollow cylindrical cavity has a cavity diameter and penetrates the distal face; an injector tip, mounted on the distal face coaxially with the axis, the injector tip comprising a hollow needle injector having a bore diameter substantially equal to the cavity diameter; a cylindrical anchor drive piston, coaxially located within the hollow cylindrical cavity, the diameter of the cylindrical anchor drive piston selected to allow axial displacement through the hollow cylindrical cavity and the bore of the hollow needle injector; and an anchor feed mechanism connected to the hollow cylindrical cavity. The suturing device may further comprise a first constriction gate positioned at the interface between the distal face of device body and the injector tip. In additional embodiments, the cylindrical anchor drive piston is hollow and defines a coaxial piston cavity; the anchor feed mechanism comprises the coaxial piston cavity and a distal face of the coaxial piston; and the anchored suture line may be preloaded within the coaxial piston cavity. A second constriction gate that is positioned at a distal face of the cylindrical anchor drive piston may also be provided.

In another embodiment, the cylindrical anchor drive piston may be solid; the device body further defines a suture feed tunnel having a circular cross-section and perpendicularly intersecting the cylindrical cavity at a location proximal to the injector tip, the diameter of the suture feed tunnel is approximately equal to the diameter of the cylindrical cavity; and the anchored suture line may be preloaded within the suture feed tunnel. The embodiments may also provide a suture cutting mechanism.

In additional embodiments, there is provided a method for performing a suture procedure comprising the steps of: obtaining an ASL suturing device preloaded with anchored suture line; inserting an injector tip of the ASL suturing device into biological tissue at a first location; injecting a first anchor structure from the ASL suturing device through the injector tip; allowing the first anchor of the anchored suture line to expand; withdrawing the injector tip from the biological tissue from the first location; inserting the injector tip into biological tissue at a second location; injecting a second anchor structure from the ASL suturing device through the injector tip; allowing the second anchor structure to expand; withdrawing the injector tip from the biological tissue from the second location; repeating steps as many times as necessary to close a wound; and cutting the anchored suture line.

DRAWINGS

The description of the non-limiting embodiments of the invention may be furthered by the following figures.

DETAILED DESCRIPTION OF EMBODIMENTS

Definitions

Figure 1:
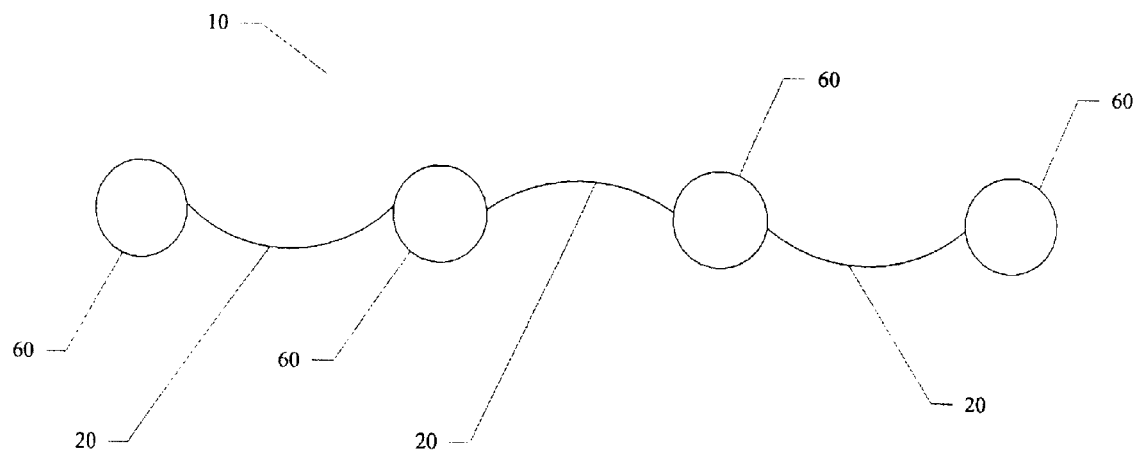
FIG. 1 is a simplified illustration of a section of a non-limiting embodiment of an anchored suture line where the anchor structures can be made to expand after implantation.

Anchor structure: An anchor structure is a self-contained mass attached to a suture line at predetermined intervals. The suture line passes through the anchor structure and defines its axis. The anchor structure can be caused to transition from a compressed state to an expanded state after insertion or injection into a biological tissue. The anchor structure is complete and does not utilize any additional fixtures, anchors, or fittings to perform its anchoring function.

Compressed state: The compressed state is the state or condition of the anchor structure where a section cut through the anchor structure, perpendicular to the suture line, has an area less than or equal to the cross sectional area of the injector needle bore.

Expanded state: The expanded state is the state or condition of the anchor structure where a section cut through the anchor structure, perpendicular to the suture line, has an area greater than the area of the injector needle bore. In its expanded state, the anchor structure cannot be withdrawn from the biological tissue. The percentage increase between the compressed and expanded state may be selected by choosing the composition of the anchor structure material. In some embodiments, the percentage increase may be between 1% and 100%. In other embodiments the percentage increase may be greater than 100%. The time required to transition from the compressed state to the expanded state may also be chosen by the composition of the anchor structure material. In some embodiments, the expansion time may be less than or equal to 10 seconds. In other embodiments the expansion time may be greater than 10 seconds.

Constriction gate: A constriction gate is a mechanical structure that serves to reduce the cross sectional area of a passageway thereby restricting the passage of an anchor structure through the passageway. The application of an axial force applied through the anchor structure causes the cross sectional area of the constriction gate to increase and/or the cross sectional area of the anchor structure to decease thereby allowing passage of the anchor structure through the constriction gate. Conversely, the constriction gate may be used to apply force to an anchor structure within the passageway thereby causing displacement of the anchor structure. In embodiments, the force required to displace the anchor structure through the constriction gate in a first direction may be equal in magnitude to that required in the reverse direction. In other embodiments, the force required to displace the anchor structure through the constriction gate in a first direction may be unequal in magnitude to that required in the reverse direction.

Distal: Situated forward.

Proximal: Situated rearward.

DETAILED DESCRIPTION

In non-limiting embodiments, an Anchored Suture Line (ASL) alternative to conventional suturing is presented. An Anchored Suture Line is comprised of a length of suture thread upon which is positioned a plurality of permanently affixed anchor structures, located at a predetermined spacing along the length of the suture thread. An ASL suturing device, having a hollow needle injector, may be preloaded with a length of the Anchored Suture Line in a configuration that permits passage of the anchored suture line through the hollow needle injector's bore.

In practice, the ASL suturing device comprising a hollow needle injector, positioned at the first stitch location, is made to penetrate the biological tissue and inject a single anchor structure tethered to the suture thread. Once implanted, the injected anchor structure is caused to cross-sectionally expand to dimensions greater than the penetration orifice thereby securing the anchor structure in the biological tissue. The needle injector may then be withdrawn leaving behind the expanded anchor structure still tethered to the suture thread. The needle injector may then be repositioned to a second stitch location and may be made to penetrate the biological tissue and a second anchor structure may be injected or deployed. The second anchor structure may be caused to cross-sectionally expand and the needle injector may be again withdrawn. This process may be repeated any number of times resulting in a continuous anchored closure suture. After the required number of sutures has been placed, the suture thread may be severed using a separate or self-contained suture thread cutter and the procedure may be concluded or a new suture line may be started.

The Anchored Suture Line suturing procedure may be performed with a single surgical instrument, the ASL suturing device, with one hand and does not require any knot tying to secure the suture. The resulting suture simultaneously provides the suture stitch independence of the conventional interrupted suture technique while offering the speed of conventional continuous closure suturing.

The suture thread material may have elastic properties and the anchor structures may be resilient so that the suture thread may maintain a desired level of tension. The use of a suture thread having elastic properties provides more freedom in selecting the suture penetration sites. In a non-limiting embodiment, a candidate elastic suture thread technology is described in U.S. Pat. No. 4,621,638 to Silvestrini and entitled Hard Elastic Sutures.

The ASL device and suture line may be appropriately sized for any surgical procedure. The device, as embodied, should have no restriction with regards to being used in macro, microsurgical or endoscopic platforms (different dimension of the ALS suture device) and should have no limitations with regards to biological tissue types that can be joined together.

The preloaded suturing device may be supplied in hermetically sealed and sterile packaging thereby minimizing the possibility of exposure of the suture to contaminating or infectious agents at any point after manufacture. Containment of the Anchored Suture Line within the injector can insure that the suture material maintains sterility.

As illustrated in FIG. 1, the Anchored Suture Line 10 is comprised of a suture thread 20 to which anchor structures 60 are permanently located at predetermined distances along its length. Each of the anchor structures 60 may be formed from a material distinct from the suture thread 20 and subsequently attached at time of manufacture or, alternatively, formed as an integral structure comprising the suture thread 20 material itself. In a non-limiting embodiment, each of the anchor structures 60 may have a spherical shape and be penetrated by the suture thread 20 along a major diameter. Alternatively, other anchor structure shapes (i.e., cylindrical, ellipsoidal, disc etc.) are also envisioned. In some embodiments, the preloaded anchored suture line may comprise two anchor structures. In other embodiments, the preloaded anchored suture line may comprise at least three anchor structures.

The suture thread may be formed of any absorbable or non-absorbable material suitable for use as suture material. The requirements placed on the suture material are relaxed in that properties necessitated by knot-security considerations are no longer required. This broadens the scope of materials that may be chosen in any situation. The suture thread may be formed, surface treated or otherwise modified, at the locations at which the respective anchors are located, to improve the attachment of the anchor structure and prevent movement along the length of the suture thread.

Each anchor structure can be caused to exhibit at least two cross-section dimensional states with respect to the plane of the puncture; a compressed state and an expanded state. In its compressed state, the cross-sectional dimensions of the anchor permit passage through the ASL suturing device's hollow needle injector. In its expanded state, the cross-sectional dimensions of the anchor structure are increased thereby preventing passage, after deployment, back through the biological tissue puncture made by the hollow needle injector. The anchor structure exhibits sufficient strength to prevent dislodgement or tearing-out of the embedded suture thread. The anchor structure may be shaped, in its expanded state, to effectively "plug" the biological tissue penetration thereby minimizing leakage of bodily fluids. In addition, the anchor's composition may be chosen to include agents that expedite hemostasis.

The anchors may be preloaded in the ASL suturing device in their compressed state. After being injected into the biological tissue, the anchors may transition to their expanded state.

In a non-limiting embodiment, the anchor structure may be formed of a resilient material that can be made to volumetrically expand when subjected to specified environmental conditions. Examples of such specified environmental conditions may include one or more of 1) immersion in or contact with bodily fluids or other liquids, 2) temperature change, 3) pressure change, 4) exposure to acoustic energy, 5) exposure to electro-magnetic energy, 6) exposure to magnetic field, and 7) exposure to electric field. The anchor structure may exhibit different resiliency properties in the compressed and expanded states.

Figure 2A:
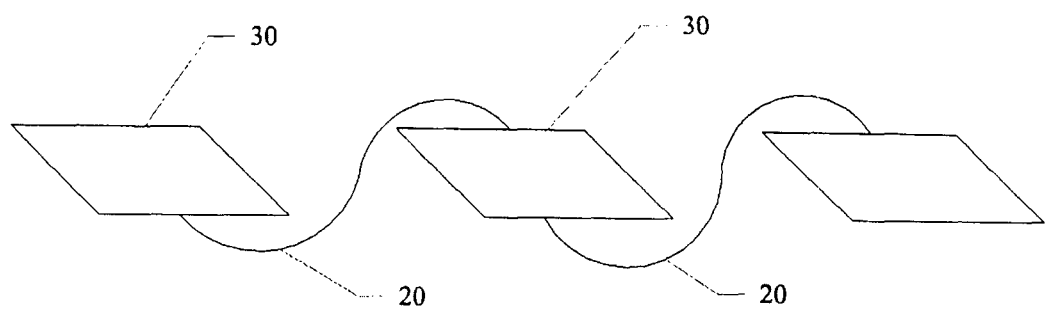
FIG. 2a is a simplified illustration of a section of a non-limiting embodiment of an anchored suture line where the anchor structures are asymmetrically shaped.
Figure 2B:
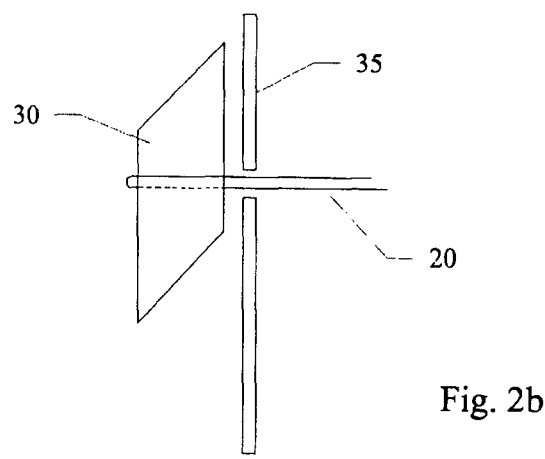
FIG. 2b is a simplified illustration of an implanted asymmetrically shaped anchor structure.

In another non-limiting embodiment, as shown in FIG. 2a, the anchor structure 30 may be formed as an asymmetrically shaped body that exhibits, in a first orientation, a cross sectional profile that may pass through the hollow needle injector. In a second orientation, a cross sectional profile of the anchor structure 30 cannot pass through the biological tissue puncture created by the hollow needle. In accordance with this non-limiting embodiment, the ASL anchors would be preloaded into the injecting device with the first orientation that permits passage through the hollow needle injector. As shown in FIG. 2b, after deployment in the biological tissue 35, the force applied by the suture thread 20 causes the anchor structure 30 to reorient itself into the second orientation thereby preventing removal of the anchor structure 30 from the biological tissue 35.

Amongst the properties of the material comprising the anchor structure are biocompatibility, absorbability/non-absorbability, and compatibility with the suture thread as would be understood by one of ordinary expertise in the field.

The anchor structure may be formed of a single homogeneous material or of two or more layers of distinct materials having different properties. For example, in a non-limiting embodiment, the anchor structure may comprise a core layer of a first material, selected to enhance adhesion with the embedded suture line, and a surface layer of a second material, selected to provide volumetric expansion.

In another non-limiting embodiment, the anchor structure may comprise a hollow surface formed of resilient material. The surface of such anchor structure may be continuous or may be comprised of a flexible frame mesh or interconnected spars. Materials, such as Nitinol, that change physical characteristics in response to environmental conditions are also envisioned.

In a non-limiting embodiment, the anchor structure may be formed from a resilient sponge or foam. In accordance with this non-limiting embodiment, the resilient sponge anchor structure may be compressed and maintained in its compressed state by the ASL suturing device. Upon implantation into the biological tissue, the removal of the physical constraint of the ASL suturing device may result in the volumetric expansion of the sponge anchor structure. The expansion may be facilitated by contact with bodily fluids present at the implantation site. One non-limiting example of a suitable resilient material is a porous hemostatic absorbable gelatin sold by Pfizer under the name Gelfoam™.

In another non-limiting embodiment, the anchor structure may be formed of a resorbable, self-expandable compressed matrix collagen based polymer that volumetrically expands on contact with bodily fluids. One such example polymer is described in U.S. Pat. No. 5,571,181, to Li, entitled "Soft Tissue Closure Systems" which is hereby incorporated by reference in its entirety. Amongst the desirable properties of that material in this application are a volumetric expansion between the compressed and expanded states of between three (3) and twenty (20) times, and a recovery time from the compressed state to the expanded state of between one (1) and sixty (60) seconds.

A second non-limiting example of a resorbable, self-expandable compressed matrix collagen based polymer is described in U.S. Patent Application Publication US 2003/0013989, and U.S. Pat. No. 8,877,233, issued Nov. 4, 2014, to Obermiller et al., entitled "Porous Sponge Matrix Medical Devices and Methods" which is hereby incorporated by reference in its entirety. This reference teaches a polymer that may provide volumetric expansions in the range of two (2) to ten (10) times and recovery times of less than ten (10) seconds while providing superior compressed state dimensional stability.

The anchored suture line may be used to close a wound by performing a suturing procedure using an ASL suturing device. The suturing device is used to penetrate the biological tissue with a hollow needle injector tip, inject a tethered anchor structure, allow the tethered anchor structure to expand, withdraw the needle injector tip, reposition the needle injector tip at the next penetration site, penetrate the biological tissue and inject the next tethered anchor structure. This process may be repeated, without cutting the suture line, until the wound is completely closed. Each of the steps of this procedure may be performed by the surgeon using a single hand and without any other tools or instruments. No knot tying is required.

Figure 3:
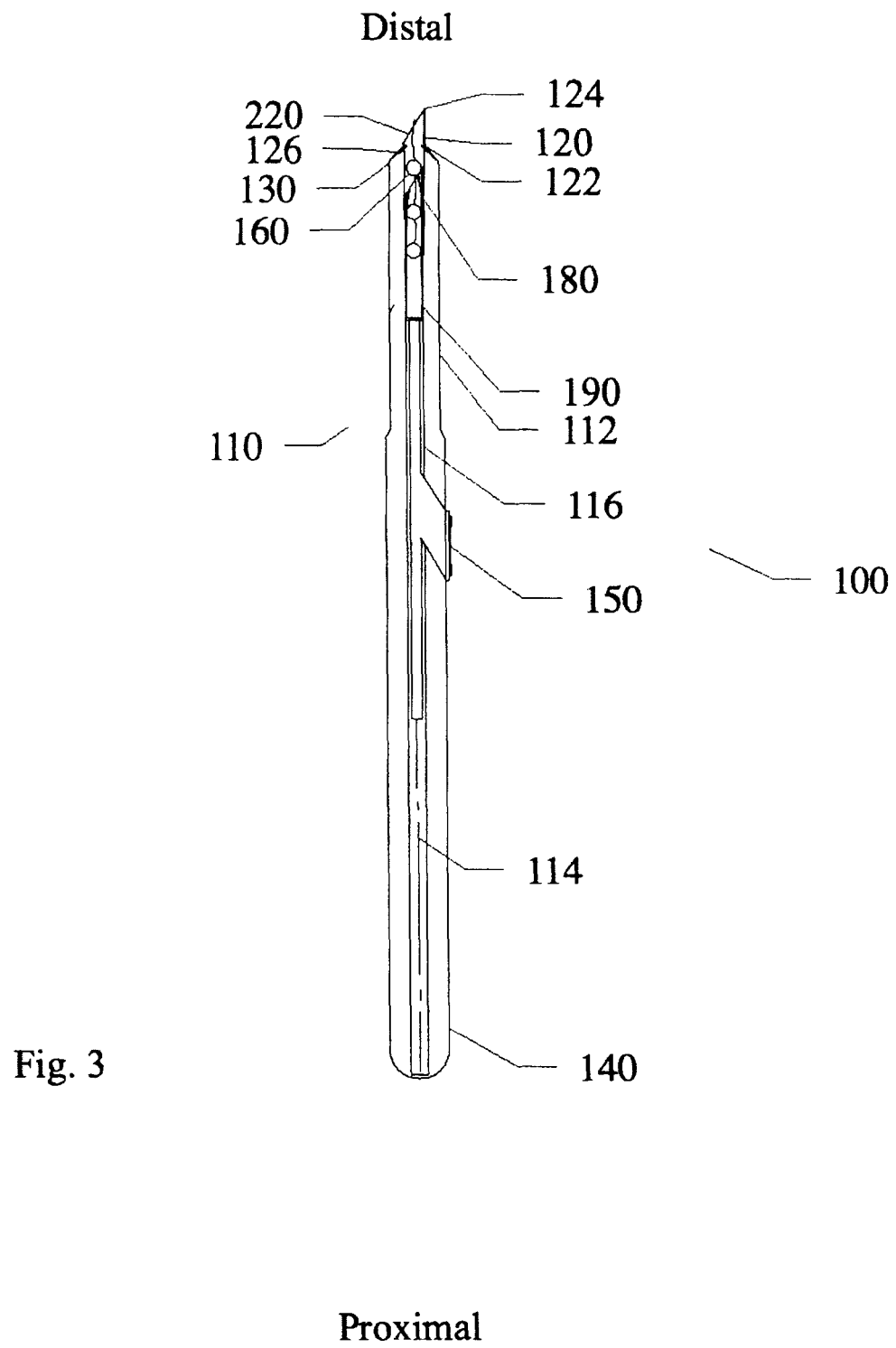
FIG. 3 is a simplified cross-sectional cutaway view of a non-limiting embodiment of an Anchored Suture Line suturing device.

FIG. 3 is a cross-sectional view (not to scale) of a non-limiting embodiment of an ASL suturing device 100. The body 110 of the ASL suturing device is ergonometricly and functionally designed for single-handed operation. As envisioned, the ASL suturing device 100 could be made available in different sizes suitable for different surgical procedures and surgeon's preferences. Having a substantially cylindrical shape, an injector tip 120 protrudes from the distal extremity 130 of the device body. The proximally located handle portion 140 of the device body may be molded and contoured for comfortable fit. The controls necessary to operate the device such as a sliding finger pad 150 may be integrated into the handle.

The ASL suturing device 100 comprises a device body 110, an injector tip 120, and a hollow anchor drive piston 190. The device body 110 has a substantially cylindrical outer surface 112 defined about a cylindrical axis 114. The device body 110 further defines a cylindrical cavity 116, coaxial with the cylindrical axis 114 that penetrates the distal body surface 130. An injector tip 120, through which the anchored suture line 180 is injected, is mounted to the distal body surface 130. The device 100 may be provided, preloaded with a length of anchored suture line 180. In a non-limiting embodiment, the anchored suture line may be provided in a cartridge. A finger operated anchor drive piston 190 may be used to push each anchor structure 160 through the injector tip 120 until it is deployed at the biological tissue injection site. The injector tip 120 comprises a hollow bore needle injector 122 with a cutting edge 124 at the distal extremity mounted on a proximal hollow conical shaped mounting collar 126. The mounting collar 126 is formed to mate with the distal body surface 130, coaxially with the cylindrical axis 114. The hollow needle's bore 220 has approximately the same cross section dimensions as the cylindrical cavity 116 of the body thereby providing a continuous cylindrical channel.

After deployment, the anchor structure 160 remains attached to the suture line 180. When the injector tip 120 is withdrawn from the biological tissue injection site and the piston 190 is retracted, the anchored suture line 180 may be used to pull the next anchor structure 160 into position at the proximal end of the injector tip 120. In some non-limiting embodiments an anchor feed mechanism (not shown) may facilitate loading of the next anchor structure. This process may be repeated until the final anchor structure 160 is deployed. Once the final anchor structure 160 is deployed, a suture cutter, either internal or external to the suture device, may be employed to cut the suture line thereby allowing disconnection of the device.

Figure 4:
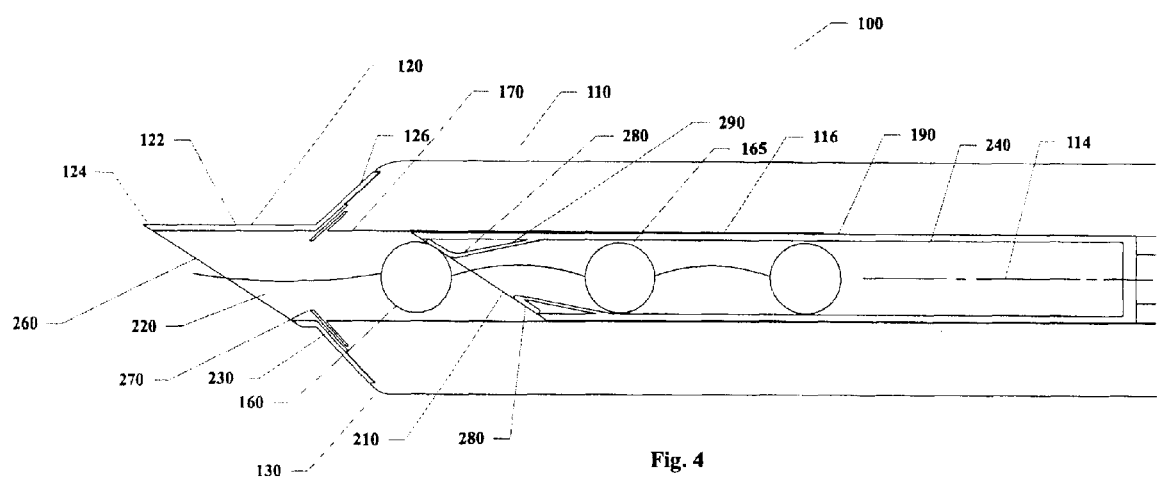
FIG. 4 is a simplified cross-sectional close-up cutaway view of a non-limiting embodiment of an Anchored Suture Line suturing device having a hollow anchor drive piston.

As seen in a close-up cutaway view of the embodiment of the ASL suturing device in FIG. 4, the hollow bore needle injector 122 axially protrudes from the distal surface 130 of the device. The exposed length of the protruding needle injector 122 may be approximately the thickness of the biological tissue layer(s) to be penetrated thereby providing a depth guide for placement of the anchor. A finger operated anchor drive piston 190 can be made to displace through the hollow bore needle injector 122 thereby pushing the anchor structure 160 out of the distal opening of the hollow bore needle injector 122. The portion of the body cylindrical cavity 116 between the proximal mounting surface 126 of the injector tip and the distal face 210 of the anchor drive piston defines a chamber 170. In its fully extended (distal) position, the distal face 210 of the anchor drive piston may be aligned with the distal opening of the hollow bore needle injector 122 thereby deploying an anchor structure 160. In its fully retracted position, the distal face 210 of the anchor drive piston may be positioned to form chamber 170 so that an anchor structure may be dispensed from the coaxial piston cavity 240 into the chamber 170.

The anchor drive piston 190 is coaxially located within the cylindrical cavity 116 of the body and is dimensioned to permit axial displacement within the body cylindrical cavity 116 and the hollow needle injector bore 220. The anchor drive piston 190 is also hollow and defines an anchor drive piston cavity 240.

A first constriction gate 230 may be provided at the interface between the distal surface 130 of the body and the proximal mating surface 120 of the injector tip. The constriction gate 230 provides a restriction to the passage of anchor structures 160 that may be overcome by force applied by the anchor drive piston 190. The restriction thereby prevents the unintended dispensing of an anchor structure 160. The constriction gate 230 may be implemented as a plurality of flexible leaves 270 that, in combination, reduces the cross sectional opening of the cylindrical cavity 116 path. The flexible leaves 270 are configured to increase the cross sectional opening sufficiently to permit passage of the anchor structure 160 when force is applied in a distal direction and to decrease the cross sectional opening when force is applied in a proximal direction. In other embodiments, the first constriction gate 230 may be implemented as a resilient "O-ring" (not shown) located around, and protruding in from the inner periphery of the cylindrical cavity 116 at the interface between the distal surface 130 of the body and the proximal mating surface 126 of the injector tip. In this embodiment, the anchor structure 160 must be forced through the "O-ring" as it is being pushed into the hollow needle injector bore 220. In other additional embodiments, that are suitable for use with anchor structures 160 having resiliency, the "O-ring" may be non-resilient. The "O-ring" may be implemented as a separate structure or as an integral part of the cylindrical cavity 116.

A second constriction gate 280 may be provided at the distal face 210 of the anchor drive piston. The second constriction gate 280 provides a tactile indication that the next anchor structure 160 is loaded in the chamber 170 and a distal face surface 210 that may be used to push the anchor structure 160 through the injector tip 120. This second constriction gate 280 may be implemented by a plurality of resilient ribs 290 located within the anchor drive piston cavity 240 in proximity to the distal face 210. These ribs 290 expand their opening at the distal face 210 of the piston when pressure is applied in the distal direction thus allowing an anchor 160 to pass. The application of pressure to the second constriction gate 280 in the proximal direction causes the opening at the distal face 210 to contract thereby permitting the anchor 160 to be pushed in the distal direction until it is injected from the distal face 260 of the needle. In other embodiments, the second constriction gate 280 may be implemented as a resilient "O-ring" (not shown) located within the anchor drive piston cavity 240 in proximity to the distal face 210. In this embodiment, the anchor structure 160 must be pulled through the "O-ring" by a force exerted by the suture thread tethered to an already implanted anchor.

Figure 5:
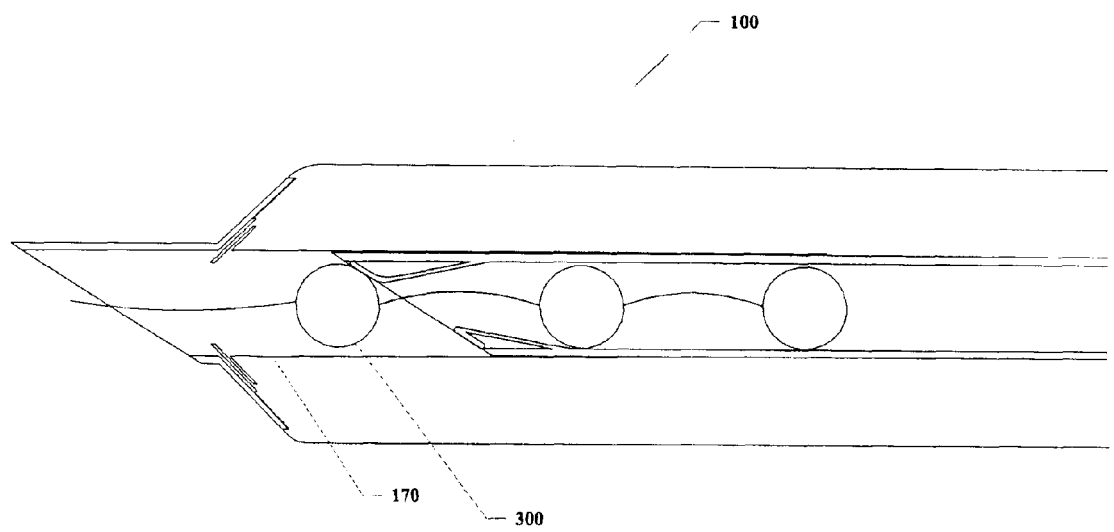
FIG. 5 is a simplified cross-sectional close-up cutaway view of a non-limiting embodiment of an Anchored Suture Line suturing device in its initial condition.
Figure 6:
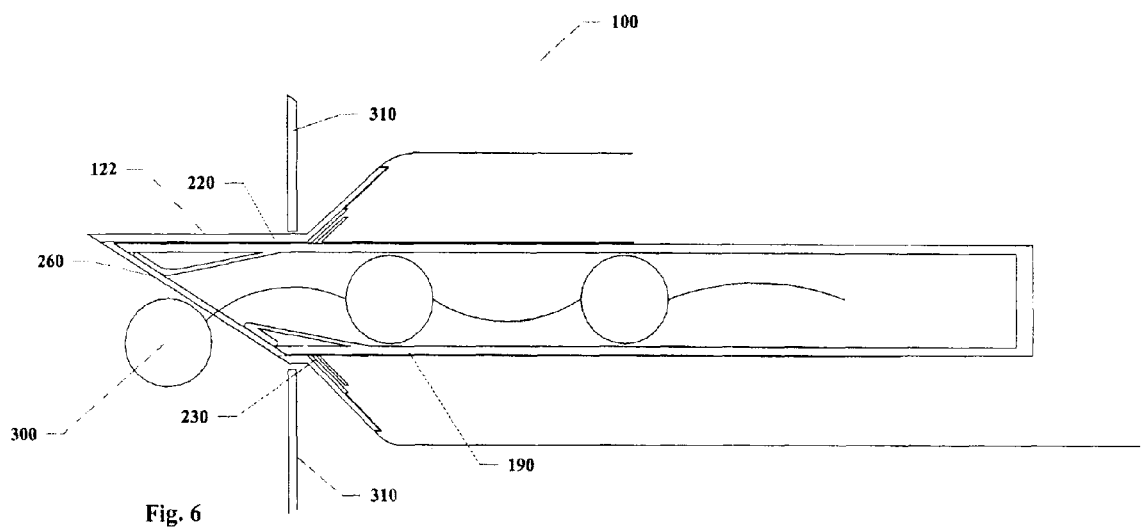
FIG. 6 is a simplified cross-sectional close-up cutaway view of a non-limiting embodiment of an Anchored Suture Line suturing device having deployed an anchor structure.
Figure 7:
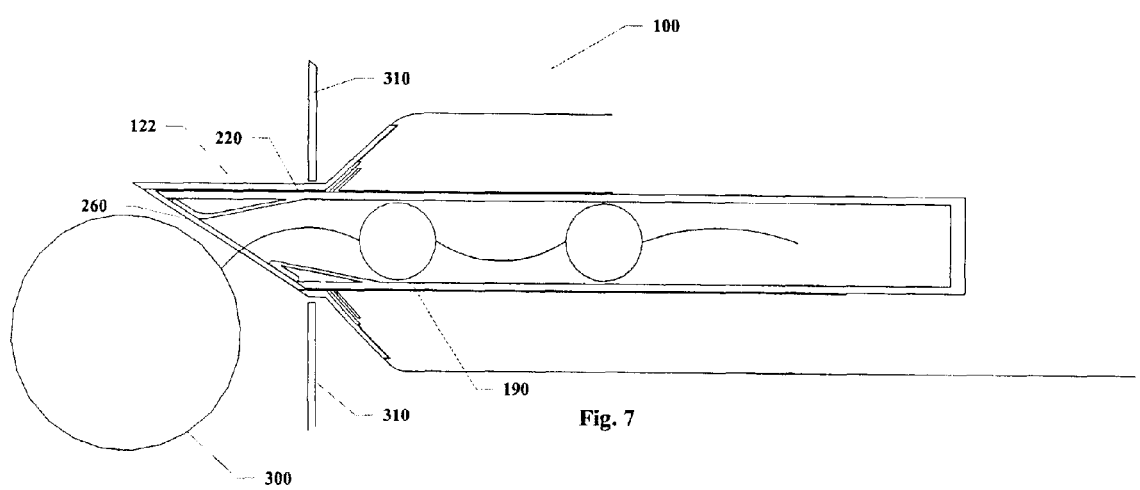
FIG. 7 is a simplified cross-sectional close-up cutaway view of a non-limiting embodiment of an Anchored Suture Line suturing device with an expanded anchor structure deployed in biological tissue.
Figure 8:
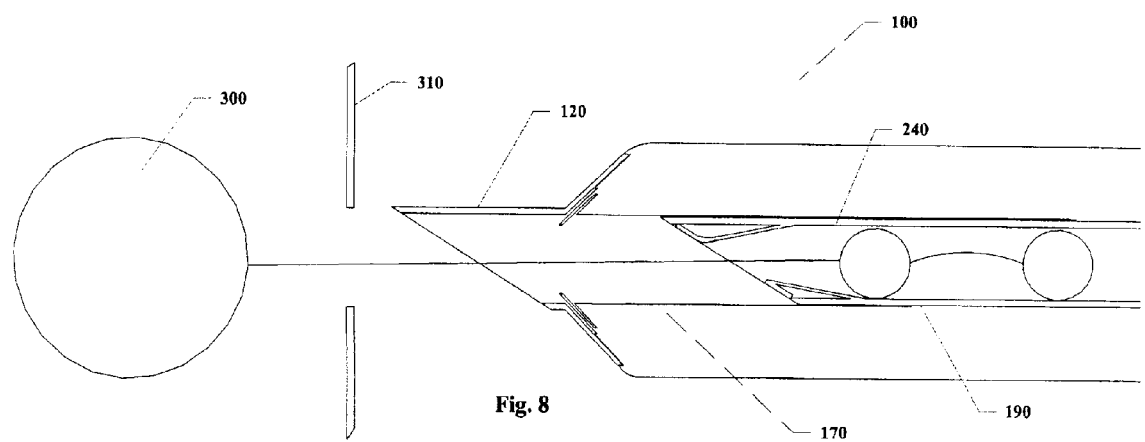
FIG. 8 is a simplified cross-sectional close-up cutaway view of a non-limiting embodiment of an Anchored Suture Line suturing device retracted from biological tissue puncture.
Figure 9:
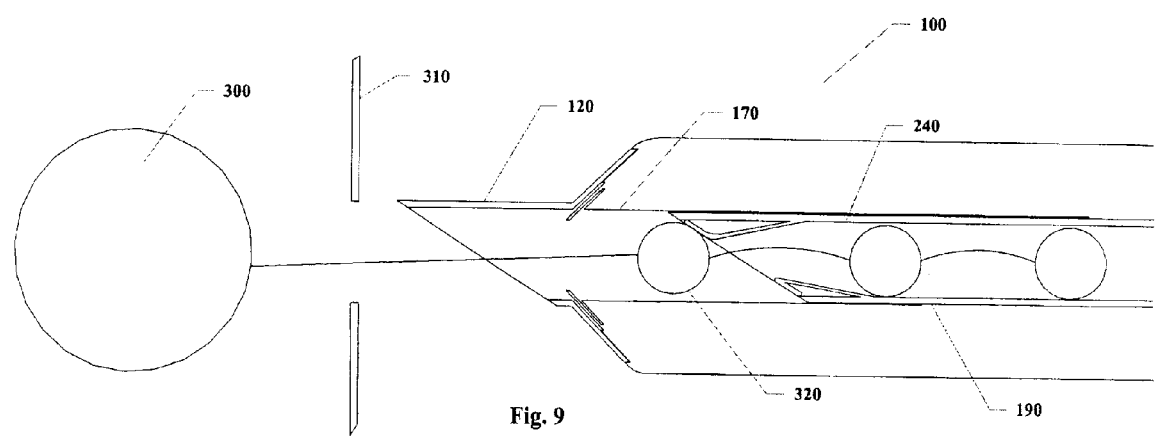
FIG. 9 is a simplified cross-sectional close-up cutaway view of a non-limiting embodiment of an Anchored Suture Line suturing device with a next anchor structure prepared for deployment.
Figure 10:
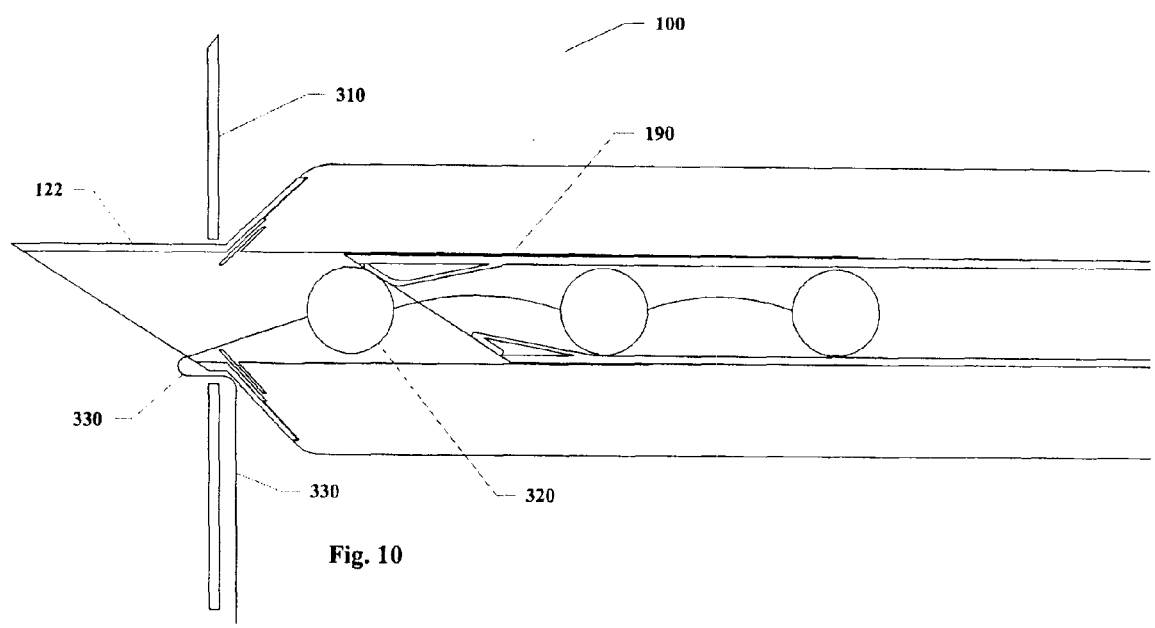
FIG. 10 is a simplified cross-sectional close-up cutaway view of a non-limiting embodiment of an Anchored Suture Line suturing device having penetrated the biological tissue at a second location showing the suture line connected to the previously deployed anchor structure and the next anchor structure ready for deployment.

The operation of the ASL suturing device is illustrated in FIGS. 5 through 10. FIG. 5 shows the suturing device 100 in its initial condition, before the first anchor structure 300 has been injected. The first anchor structure 300 is seen loaded into the chamber 170. In FIG. 6, the hollow bore needle injector 122 has been made to penetrate the biological tissue 310 at a first location and the anchor drive piston 190 has been advanced in the distal direction pushing the first anchor structure 300 past the first constriction gate 230, through the hollow needle injector bore 220, and out the distal face of the hollow bore needle injector 260. In FIG. 7, the deployed first anchor structure 300 is seen to expand thereby anchoring the suture in the biological tissue. In FIG. 8, the injector tip 120 has been withdrawn from the biological tissue 310 and the anchor drive piston 190 has been retracted thereby again creating the chamber 170. In FIG. 9, the ASL suturing device 100 is further withdrawn thereby pulling the second anchor structure 320 from the anchor drive piston cavity 240 into the chamber 170. In FIG. 10, the hollow bore needle injector 122 is made to penetrate the biological tissue 310 at the second location and the anchor drive piston 190 may be advanced in the distal direction to deploying the second anchor 320. The suture line 330 may be seen as still being attached to the previously implanted anchor structure (not shown). This process may be repeated as many times as necessary, without cutting the suture line, to complete closure of the wound.

Figure 11:
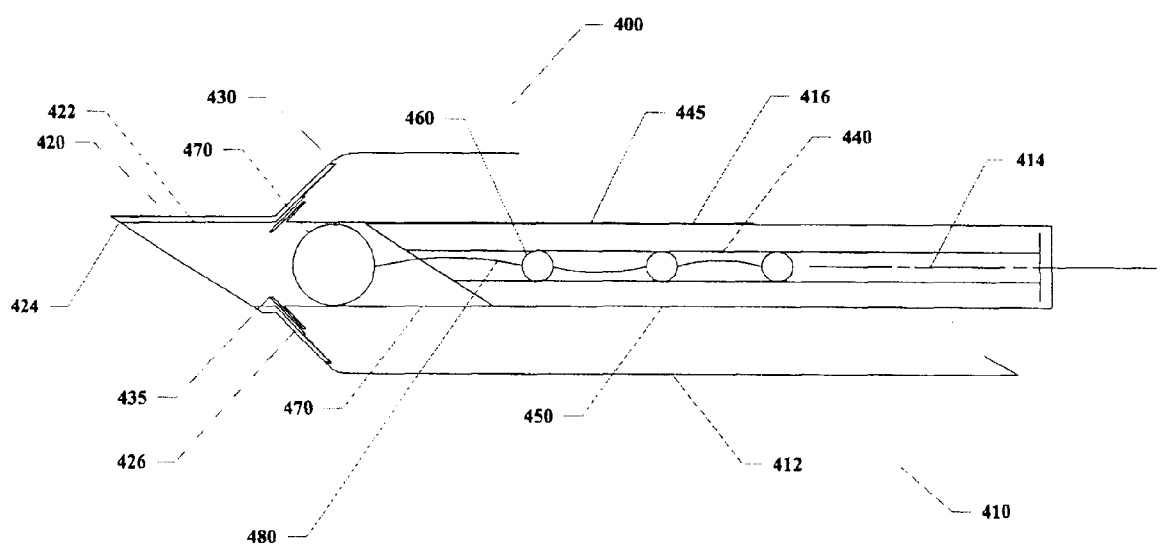
FIG. 11 is a simplified cross-sectional close-up cutaway view of another embodiment of a non-limiting embodiment of an Anchored Suture Line suturing device having a thick walled hollow anchor drive piston.

In another non-limiting embodiment, the ASL suturing device 400, as shown in FIG. 11, comprises a device body 410, an injector tip 420, and a hollow anchor drive piston 445. The device body 410 has a substantially cylindrical outer surface 412 defined about a cylindrical axis 414. The device body 410 further defines a cylindrical cavity 416, coaxial with the cylindrical axis 414 that penetrates the distal body surface 430. An injector tip 420 through which the anchored suture line 480 is injected is mounted to the distal body surface 430. The device 400 may be provided, preloaded with a length of anchored suture line 480. A finger operated anchor drive piston 440 may be used to push each anchor structure 460 through the injector tip 420 until it is deployed at the biological tissue injection site. The injector tip 420 comprises a hollow bore needle injector 422 with a cutting edge 424 at the distal extremity and a proximal mating surface 426 formed to mate with the distal body surface 430, coaxially with the cylindrical axis 414. The hollow needle's bore 420 has approximately the same cross section dimensions as the cylindrical cavity 416 of the body thereby providing a continuous cylindrical channel. As was the case for the previous embodiment, a first constriction gate 435 may be provided at the interface between the distal surface 430 of the body and the proximal mating surface 426 of the suture injector.

In accordance with this embodiment, the anchor drive piston 445 is hollow with thickened walls 450 (as compared to the previous embodiment) that define an anchor drive piston cavity 440 having a diameter significantly less than that of the body cylindrical cavity 416. The anchor drive piston cavity 440 may be preloaded with an anchored suture line comprising resilient anchors 460 that are compressed to fit into the reduced diameter anchor drive piston cavity 440. Pulling an anchor structure 460 into the chamber 470, by means of the suture line secured to a previously deployed anchor, permits the anchor structure 460 to partially expand to the diameter of the body cylindrical cavity 416. The thickened walls 450 are of a dimension that provides a distal face surface area that is sufficient to push the partially expanded anchor structure 460 from the chamber 470 through the hollow needle injector bore 422. In a non-limiting embodiment the thickened walls 450 form a solid portion of the distal face having an area of less than 10% of the total area of the distal face. In another non-limiting embodiment, the thickened walls 450 form a solid portion of the distal face having an area of 10% or greater but less than 90% of the total area of the distal face. In a further non-limiting embodiment, the thickened walls 450 form a solid portion of the distal face having an area of 90% or more of the total area of the distal face. Once deployed through the hollow needle injector bore 422, the partially expanded anchor structure 460 may fully expand in the biological tissue.

Figure 12:
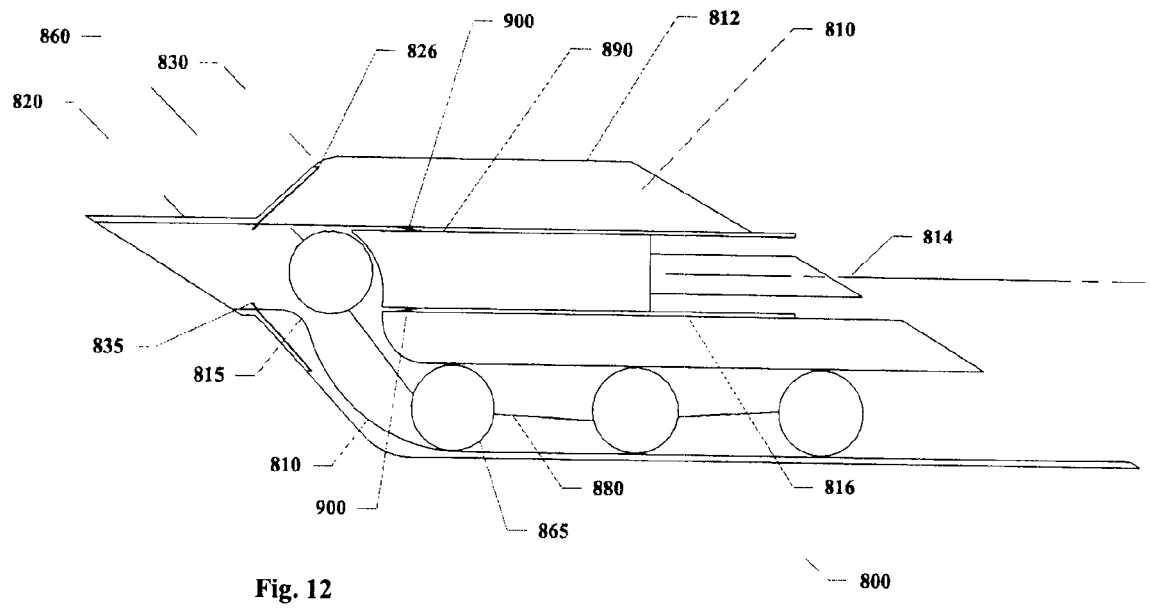
FIG. 12 is a simplified cross-sectional close-up cutaway view of another embodiment of a non-limiting embodiment of an Anchored Suture Line suturing device having a solid anchor drive piston and a suture feed tunnel and an internal suture line cutter.

In another non-limiting embodiment of the ASL suturing device 800, as shown in FIG. 12, comprises a device body 810, an injector tip 820, and a solid anchor drive piston 840. The device body 810 may have a substantially cylindrical outer surface 812 defined about a cylindrical axis 814. The device body 810 further defines a cylindrical cavity 816, coaxial with the cylindrical axis 814 that penetrates the distal body surface 430. The device body 810 further defines a suture feed tunnel 810, having a circular cross-section and perpendicularly intersecting the cylindrical cavity 816 at a location proximal of the injector tip 820. The path of the suture feed tunnel 810 may smoothly transition from being perpendicular to the cylindrical cavity 816 to being parallel. Throughout it length, the circular cross section diameter of the suture feed tunnel 810 should remain approximately constant so that the movement of anchors is not impeded. As with the previous embodiments, a first constriction gate 835 may be provided at the interface between the distal surface 830 of the body and the proximal mating surface 826 of the suture injector.

The suture feed tunnel 810 may be pre-loaded with the anchored suture line 880. An injector tip 420 through which the anchored suture line 480 is injected is mounted to the distal body surface 830. A finger operated anchor drive piston 890 may be used to push each anchor structure 860 through the injector tip 820 until it is deployed at the biological tissue injection site. In this embodiment, the diameter of the anchor drive piston 890 is selected to permit the suture thread to pass between the anchor drive piston 890 and the walls of the cylindrical cavity 816. The injector tip 820 comprises a hollow bore needle injector 822 with a cutting edge 824 at the distal extremity and a proximal mating surface 826 formed to mate with the distal body surface 830, coaxially with the cylindrical axis 814. The hollow needle's bore 822 has approximately the same cross section dimensions as the cylindrical cavity 816 of the body thereby providing a continuous cylindrical channel.

In operation, the solid anchor drive piston 890, may be initially positioned as shown in FIG. 12, with a first anchor structure 860 positioned in the cylindrical cavity 816. After puncturing the biological tissue at the desired location, with the injector tip 820, the piston 840 may be displaced in a distal direction thereby deploying the anchor structure 860. The ASL suturing device 800 is withdrawn from the biological tissue leaving the deployed anchor structure implanted in the biological tissue. The solid anchor drive piston 840 may then be proximally refracted to the position shown in FIG. 12. The suture line, anchored by the implanted anchor structure, may be used to pull the next anchor structure 865 into position in the cylindrical cavity 816 for subsequent deployment.

In a non-limiting embodiment, the ASL suturing device 100, may further comprise a suture cutter 900. The suture cutter 900 may be located coaxially with the anchor drive piston 840 and may be displaced by a separate finger pad. When the final anchor structure has been deployed, the suture cutter 900 may be made to drive across the mouth of the suture feed tunnel 810 thereby severing the suture line.

While the invention has been described with respect to preferred embodiments, those skilled in the art will readily appreciate that various changes and/or modifications can be made to the invention without departing from the spirit or scope of the invention as defined by the appended claims. All documents cited herein are incorporated by reference herein in their entirety for teachings of additional or alternative details, features and/or technical background.

We claim:

1. A suturing apparatus comprising:
    an anchored suture line, configured to perform suturing, and formed of a first bio-compatible suture thread upon which is located at least three anchor structures permanently attached to said first bio-compatible suture thread and longitudinally spaced at predetermined intervals along the first bio-compatible suture thread, wherein each of said at least three anchor structures is complete and does not utilize any additional fixtures, anchors, or fittings to perform its anchoring function, and said at least three anchor structures are comprised of a second bio-compatible material, distinct from said first bio-compatible suture thread, that can be caused to transition from a compressed state to an expanded state after implantation in biological tissue; and
    a suturing device, preloaded with said anchored suture line, and configured to permit a healthcare provider to single-handedly perform continuous suturing of wounds, wherein the first bio-compatible suture thread comprises stitches that penetrate said biological tissue at a succession of laterally displaced tissue puncture locations, said suturing device comprising:
    a device body;
    an injector tip fixedly attached to said device body, said injector tip comprises a hollow needle injector through which said at least three anchor structures may pass; and
    an anchor feed mechanism contained within said device body configured to feed one of said at least three anchor structures into said hollow needle injector, at each of said succession of laterally displaced tissue puncture locations.

2. The suturing apparatus, in accordance with claim 1, wherein said expanded state has a greater cross-sectional area than said compressed state.

3. The suturing apparatus, in accordance with claim 2, wherein said at least three anchor structures are formed of a resilient sponge or foam.

4. The suturing apparatus, in accordance with claim 2, wherein said at least three anchor structures are formed of a material that volumetrically expands when brought into contact with a fluid.

5. The suturing apparatus, in accordance with claim 4, wherein said material that volumetrically expands is a collagen based polymer.

6. The suturing apparatus, in accordance with claim 1, wherein said at least three anchor structures are formed of two or more layers of distinct bio-compatible materials.

7. The suturing apparatus, in accordance with claim 1, wherein:
said at least three anchor structures have an asymmetrical shape; and
said transition from said compressed state to said expanded state is achieved by reorientation of said at least three asymmetrically shaped anchor structures.

8. The suturing apparatus, in accordance with claim 1, wherein said first bio-compatible suture thread is elastic.

9. The suturing apparatus, in accordance with claim 1, wherein:
said device body has a substantially cylindrical shape with distal and proximal faces, said device body defines a hollow cylindrical cavity about an axis of said substantially cylindrical shape, said hollow cylindrical cavity has a cavity diameter and penetrates said distal face;
said hollow needle injector has a bore with a diameter substantially equal to said cavity diameter;
a cylindrical anchor drive piston, coaxially located within said hollow cylindrical cavity, a diameter of said cylindrical anchor drive piston selected to allow axial displacement through said hollow cylindrical cavity and said bore of hollow needle injector; and
said anchor feed mechanism is connected to said hollow cylindrical cavity.

10. The suturing apparatus, in accordance with claim 9, further comprising a first constriction gate positioned proximally to said injector tip wherein:
said first constriction gate is a mechanical structure that serves to reduce the cross sectional area of a passageway thereby restricting the passage of said at least three anchor structures through said passageway, and an application of an axial force, applied to said first constriction gate in a direction through said at least three anchor structures, causes the cross sectional area of said first constriction gate to increase thereby allowing passage of said at least three anchor structures through said first constriction gate, said axial force required to displace said at least three anchor structures through said first constriction gate in a first direction may be unequal in magnitude to said axial force required in a second direction.

11. The suturing apparatus, in accordance with claim 9, wherein:
said cylindrical anchor drive piston is hollow and defines a coaxial piston cavity;
said anchor feed mechanism comprises said coaxial piston cavity and a distal face of said cylindrical anchor drive piston; and
said anchored suture line preloaded within said coaxial piston cavity.

12. The suturing apparatus, in accordance with claim 11, further comprising a second constriction gate positioned at said distal face of said cylindrical anchor drive piston wherein:
said second constriction gate is a mechanical structure that serves to reduce the cross sectional area of a passageway thereby restricting the passage of said at least three anchor structures through said passageway, and an application of an axial force, applied to said second constriction gate in a direction through said at least three anchor structures causes the cross sectional area of said second constriction gate to increase thereby allowing passage of said at least three anchor structures through said second constriction gate, said axial force required to displace said at least three anchor structures through said second constriction gate in a first direction may be unequal in magnitude to said axial force required in a second direction.

13. The suturing apparatus, in accordance with claim 9, further comprising a suture cutting mechanism.

* * * * *